United States Patent [19]

Takahashi et al.

[11] Patent Number: 5,116,748
[45] Date of Patent: May 26, 1992

[54] PROCESS FOR THE PRODUCTION OF L-ALANINE DEHYDROGENASE FROM 78-3 FERM BP-2517

[75] Inventors: Mamoru Takahashi; Shinobu Nagasawa; Shigeru Ikuta; Kazuo Matsuura, all of Shizuoka, Japan

[73] Assignee: Toyo Jozo Kabushiki Kaisha, Shizuoka, Japan

[21] Appl. No.: 413,431

[22] Filed: Sep. 26, 1989

[30] Foreign Application Priority Data

Sep. 27, 1988 [JP] Japan .................. 63-241537

[51] Int. Cl.$^5$ .................. C12N 9/02; C12N 1/12
[52] U.S. Cl. .................. 435/189; 435/252.1
[58] Field of Search .................. 435/189, 252.1

[56] References Cited

U.S. PATENT DOCUMENTS 3,262,862 7/1966 Kitahara .................. 435/134

FOREIGN PATENT DOCUMENTS 59-132889 1/1983 Japan .
58-212782 12/1983 Japan .
60-180580 2/1984 Japan .
59-055186 3/1984 Japan .
60-184393 3/1984 Japan .
60-180590 9/1985 Japan .
62-036196 2/1987 Japan .

OTHER PUBLICATIONS

"Thermostable Amino Acid Dehydrogenases: Applications and Gene Cloning", *Trends in Biotechnology*, vol. 7, No. 8, Aug. 1989, by T. Ohshima et al., pp. 210–214.
Nagata et al., Biochimie, 71(4), pp. 559–564, 1989.
*Bergey's Manual of Systematic Bacteriology*, vol. 2, p. 1127.

*Primary Examiner*—David M. Naff
*Assistant Examiner*—Mike Meller
*Attorney, Agent, or Firm*—Young & Thompson

[57] ABSTRACT

A process for the production of L-alanine dehydrogenase which comprises culturing an L-alanine dehydrogenase producing microorganism belonging to the genus Sporolactobacillus in a nutrient medium and isolating thus-produced L-alanine dehydrogenase from the cultured mass. The microorganism is for example Sporolactobacillus sp. 78-3 FERM BP-2517 and mutants and variants thereof having the ability to produce L-alanine dehydrogenase in recoverable amounts. This strain is a thermophile which cannot grow at 40° C. but can grow at 45° C. and 52° C. The strain can assimilate glucose and produce lactic acid and acetic acid.

1 Claim, 6 Drawing Sheets

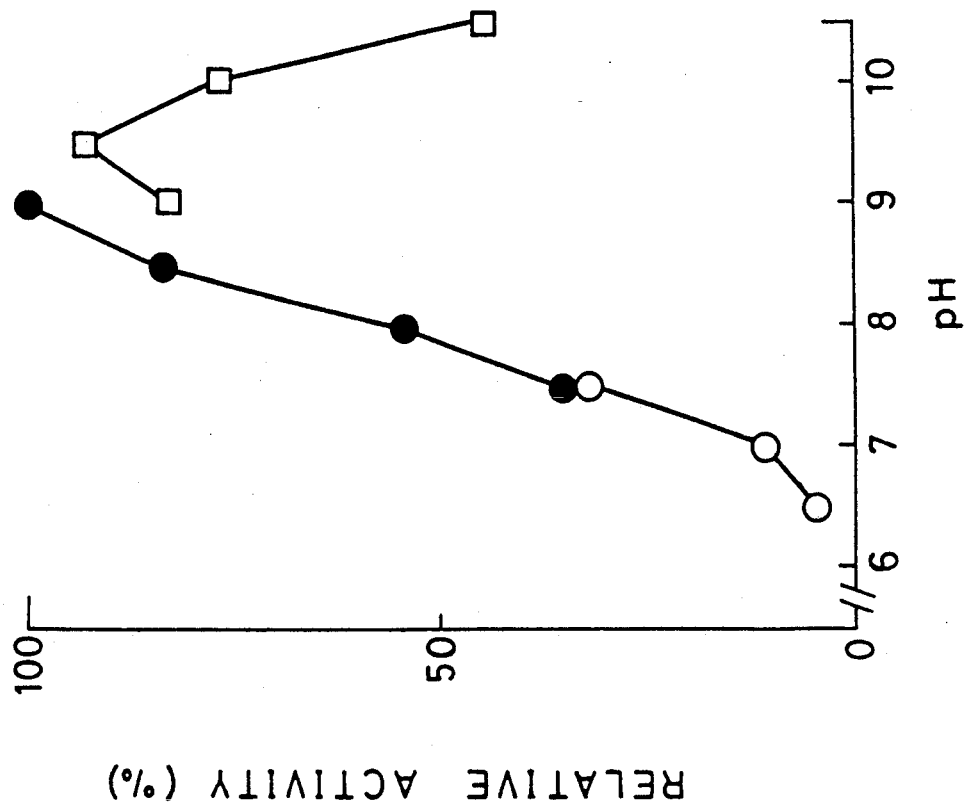
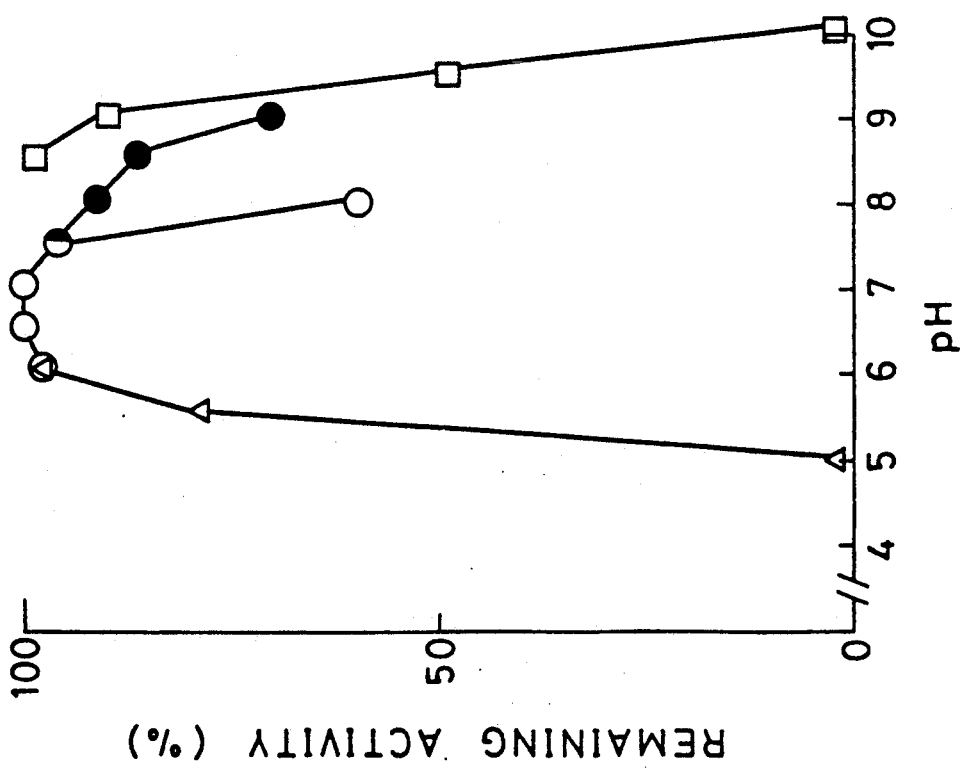

PROCESS FOR THE PRODUCTION OF L-ALANINE DEHYDROGENASE FROM 78-3 FERM BP-2517

FIELD OF THE INVENTION

This invention relates to a process for production of L-alanine dehydrogenase and a novel microorganism strain belonging to genus Sporolactobacillus.

THE PRIOR ART

L-alanine dehydrogenase is an enzyme which catalyzes the reaction (I)

L-alanine dehydrogenase has been used for quantitative measurement of pyruvate or ammonium ion directly by measuring the decrease of NADH, and has also been used for the production of L-alanine (Japanese Patent Unexam. Publ. No. 60-184393 and ibid. 62-36196). Hitherto-known production processes of alanine are a process using microorganisms belonging to the genus Thermus (Japanese Patent Unexam. Publ. No. 58-212782 and ibid. 59-55186), a process using microorganisms belonging to the genus Bacillus (Japanese Patent Unexam. Publ. No.60-180580 and ibid. 60-180590) and a process using microorganisms belonging to the genus Streotomyces (Japanese Patent Unexam. Publ. No. 59-132889).

SUMMARY OF THE INVENTION

We have found a novel microorganism strain belonging to the genus Sporolactobacillus isolated from a soil sample from a hot spring in Kumamoto Prefecture, Japan, and have found an efficient process for the production of L-alanine dehydrogenase by culturing the said novel micro-organism strain and separating thus-produced L-alanine dehydrogenase from the cultured mass.

OBJECTS OF THE INVENTION

An object of the present invention is to provide a process for the production of L-alanine dehydrogenase which comprises culturing an L-alanine dehydrogenase producing microorganism belonging to the genus Sporolactobacillus in a nutrient medium and isolating thus-produced L-alanine dehydrogenase from the cultured mass.

Another object of the present invention is to provide a novel microorganism strain belonging to the genus Sporolactobacillus wherein the said strain is a thermophile which cannot grow at 40° C. but can grow at 45° C. and 52° C.

BRIEF DESCRIPTION OF THE DRAWINGS

FIG. 3 is a graph of the pH-stability of L-alanine dehydrogenase;

FIG. 4 is a graph of the optimum pH of L-alanine dehydrogenase;

DETAILED DESCRIPTION OF THE INVENTION

Figure 2:
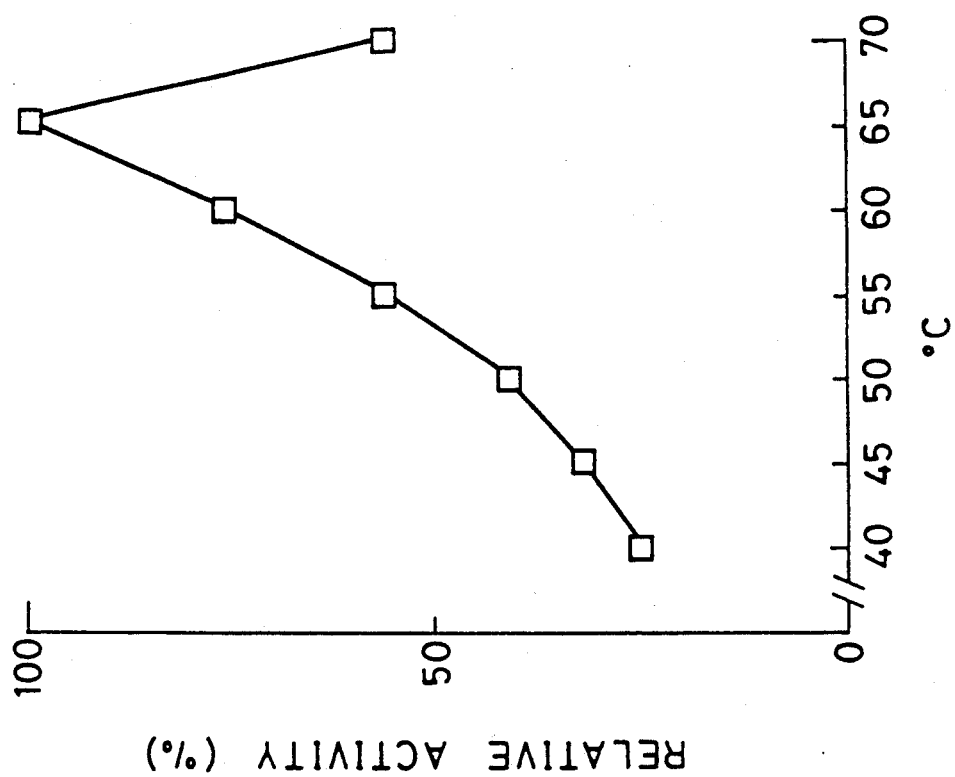
FIG. 2 is a graph of the optimum temperature of L-alanine dehydrogenase.

The taxonomical properties of the novel microorganism strain belonging to the genus Sporolactobacillus are illustrated as follows:

A. Morphological properties
 1. Form and arrangement
 Round edge with straight or slightly curved bacillus and single or double linked somewhat some chain.
 2. Size
 0.6–0.8×2.0–4.0 μm.
 3. Mobility
 Peritrichal movement.
 4. Spore
 Spore formation, but cells not bulged.
 5. Polymorphism
 Tadpole-like cells appear upon 15–20 hours culture and form a mixture of rod-shaped cells and spherical cells.

B. Macroscopic observation
 1. Nutrient agar slant medium
 Growth: weak, filiform.
 Color: transparent, ocherous.
 Soluble pigment: no production.
 2. Nutrient agar plate medium
 Growth: weak, round and flat-convex smooth and small colony.
 Color: transparent, ocherous.
 Soluble pigment: no production.
 3. Liquid medium
 Weak growth with uniform turbidity.
 4. BCP milk medium
 No change.

C. Physiological and biochemical properties (+=positive; −=negative; (+)=weakly positive):

| | |
|---|---|
| Gram-stain | + |
| KOH reaction | − |
| Acid fastness stain | − |
| Capsule formation | − |
| OF-test (Hugh Leifson) | No change |
| Aerobic growth | (+) |
| Anaerobic growth | − |
| Growth temperature | |
| 52° C. | + |
| 45° C. | + |
| 40° C. | − |
| Halotolerant NaCl conc. % | |
| 0% | + |
| 2.0% | + |
| 3.5% | − |
| Growth pH | |
| pH 9.8 | − |
| pH 9.0 | + |
| pH 5.2 | + |
| pH 4.1 | − |
| Catalase production | − |
| Oxidase production | − |
| Urease production | − |
| Gelatin hydrolysis | No change |
| Starch hydrolysis | − |
| Casein hydrolysis | No change |
| Esculin hydrolysis | + |
| Cellulose hydrolysis | − |
| Indol production | − |
| H$_2$S production | − |
| Acetoin production | − |

-continued

| | |
|---|---|
| MR test | − |
| Sulfate reduction | − |
| (Utilization test) | |
| Citrate | − |
| Malate | − |
| Maleate | − |
| Malonate | − |
| Propionate | − |
| Gluconate | − |
| Succinate | − |
| (Acid formation from sugar) | |
| Adonitol | − |
| L(+)-arabinose | − |
| Cellobiose | − |
| Dulsitol | − |
| Meso-erythritol | − |
| Fructose | + |
| Galactose | (+) |
| Glucose | + |
| Glycerin | (+) |
| Inositol | − |
| Inulin | − |
| Lactose | − |
| Maltose | + |
| Mannitol | − |
| Mannose | (+) |
| Melibiose | − |
| Raffinose | − |
| L(+)-rhamnose | − |
| D-ribose | + |
| Salicin | − |
| L-sorbose | − |
| Sorbitol | − |
| Starch | + |
| Saccharose | + |
| Xylose | (+) |
| Trehalose | + |
| (Main production of acid from) | |
| Glucose | lactic acid, acetic acid |

The media and culture conditions used hereinabove are as follows:

Basic medium: Tryptosoy broth (Difco 0370-01-1) to which is added yeast extract 0.5%.

Growth temperature: standing culture at 40° C., 45° C. and 520° C.

Growth: shaking culture.

Gelatin hydrolysis: basic medium+gelatin 0.4%+agar 1.5%, cultured in Petri dish.

BCP milk medium: basic medium+skimmed milk 10%, BCP 1% (0.2% aqueous solution), shaking culture.

Casein hydrolysis: basic medium+skimmed milk 10% +agar 1.5%, cultured in Petri dish.

Esculin hydrolysis: basic medium+esculin 1.0%+agar 1.5%+ammonium ferrous citrate 1.0% (10% aqueous solution), slant cultured.

Cellulose hydrolysis: basic medium with filter paper, shaking culture.

Acetoin production: basic medium+glucose 1.0%, shaking culture.

MR test: pH measured in medium for acetoin production (MRpH test paper).

$H_2S$ production: standing culture with basic medium. Detection using lead acetate paper.

Nitrate reduction: basic medium+$NaNO_3$ 0.1%, shaking culture.

Utilization of organic salt: basic medium+organic salt 0.3%, shaking culture. pH measured by pH meter.

Acid formation from sugar: sugar 1.0% added to a medium consisting of Trypton 1.7%, Soyton 0.3%, NaCl 0.5% and yeast extract 0.5% (pH 7.0), shaking culture. pH measured by pH meter.

Urease production: filter-sterilized urea added to the basic medium, shaking culture.

According to the above taxonomical properties, the novel microorganism strain of the present invention has the specific features of a Gram positive microaerophilic bacillus, namely, it is catalase negative and produces lactic acid and acetic acid from glucose. Furthermore, it is a thermophile not growing at 40° C. under the culture conditions hereinbefore but growing at 45° C. and 52° C.

Consulting "Bergey's Manual of Systematic Bacteriology", Vol. 2, spore-forming bacteria are illustrated in six genera having he specific features hereinbelow:

1. Genus Bacillus: aerobic or facultative anaerobic, catalase positive bacillus.

2. Genus Sporolactobacillus: Microaerophilic, catalase negative bacillus.

3. Genus Clostridium: anaerobic, catalase negative bacillus.

4. Genus Desulfotomaculum: anaerobic, catalase negative bacillus.

5. Genus Sporosarcina: aerobic, catalase positive

6. Genus Oscillospira: anaerobic, large bacillus.

The present microorganism strain shows weak growth under aerobic conditions, and is a microaerophilic and catalase negative bacillus, and so is determined to belong to the genus Sporolactobacillus. *Sporolactobacillus inulinus* is only one species of this genus which is described in "Bergey's Manual of Systemic Bacteriology", Vol. 2, and no species like the present invention has been found in "International Journal of Systematic Bacteriology", Vol. 1, 1988.

The taxonomic properties of *Sporolactobacillus inulinus* (*S. inulinus*) in comparison with those of the present strain are as follows:

| | *S. inulinus* Mainly lactic acid | The Present Strain Lactic acid/ Acetic acid |
|---|---|---|
| (Acid from glucose) | | |
| Catalase production | − | − |
| Oxidase production | − | − |
| Nitrate reduction | − | − |
| Indol production | − | − |
| (Acid formation from sugar) | | |
| Fructose | + | + |
| Glucose | + | + |
| Inulin | + | − |
| Maltose | + | + |
| Mannose | + | + |
| Raffinose | + | − |
| Saccharose | + | + |
| Trehalose | + | + |
| Mannitol | + | − |
| Sorbitol | + | − |
| Arabinose | − | − |
| Xylose | − | − |
| Galactose | − | (+) |
| Lactose | − | − |
| Melibiose | − | − |
| Cellobiose | − | − |
| Starch | − | + |
| Glycerin | − | (+) |
| Erythritol | − | − |
| Adonitol | − | − |
| Rhamnose | − | − |
| Salicin | − | − |
| Growth temperature | 15–40° C. | >45° C. |

(+ = positive; − = negative; (+) = weakly positive)

According to the above comparison, the present strain and *S. inulinus* have specific differences as to growth temperature and acid formation from glucose. Accordingly, the present strain is determined to be a novel strain belonging to the genus Sporolactobacillus and has been designated Sporolactobacillus sp. 78-3. This strain has been deposited in the permanent culture collection of the Fermentation Research Institute and assigned FERM BP-2517.

In a process for the production of L-alanine dehydrogenase of the present invention, L-alanine dehydrogenase producing microorganisms belonging to the genus Sporolactobacillus can be used. A preferred example is the aforementioned novel strain of microorganism belonging to the genus Sporolactobacillus.

L-alanine dehydrogenase producing microorganisms belonging to genus Sporolactobacillus can be cultured by conventional culture processes for antibiotics or enzyme production. Liquid or solid culture can be carried out. On an industrial scale, L-alanine dehydrogenase producing microorganisms belonging to the genus Sporolactobacillus are inoculated into a suitable growth medium and cultured under submerged aeration conditions.

Nutrient sources for the medium are conventional media for microorganism cultivation. Preferred carbon sources are assimilable carbon sources, for example carbohydrates such as glucose, saccharose, lactose, galactose, maltose, mannitol, sorbitol, dextrin, molasses or soluble starch, and various organic acids. Nitrogen sources are assimilable nitrogen sources such as peptones, powdered yeast extract, meat extract, soybean powder and casein hydrolyzate. Various kinds of salts such as phosphates, magnesium, calcium, potassium, sodium, zinc, iron, manganese or halogen, and vitamins can preferably be used.

The culture temperature can be varied depending on the growth rate of the microorganisms and the rate of L-alanine dehydrogenase production, and is 45°–60° C., preferably about 52° C. The culture time depends on the conditions and is usually 1–3 days. Cultivation should be terminated at the stage of maximum production of the enzyme.

L-alanine dehydrogenase is isolated from the thus-obtained cultured mass. An example of enzyme isolation is that the culture medium is treated by filtration or centrifugation to separate microbial cells and the isolated bacterial cells are treated with ultrasonication, French press, mechanical disruption using glass beads or freezing disruption, or is enzymatically digested with a lysozyme to obtain a crude L-alanine dehydrogenase solution. L-alanine dehydrogenase can be obtained from the crude enzyme solution by known means for the isolation and purification of proteins and enzymes. For example, a fractional precipitation method by adding an organic solvent such as acetone, methanol, ethanol or isopropanol, or salting-out by adding ammonium sulfate, sodium sulfate, potassium phosphate or ammonium aluminum to the crude solution containing L-alanine dehydrogenase can be used. Furthermore, the precipitate can be purified, if necessary, by using also a molecular sieve, chromatography, electrophoresis or ultracentrifugation. Purification can be performed by making use of the physico-chemical properties of L-alanine dehydrogenase. For example, the enzyme precipitate is dissolved in water or a buffer solution, dialyzed with a semi-permeable membrane if required, and subjected to ion-exchange chromatography using DEAE-cellulose, DEAE-Sephacel, DEAE-Sepharose, DEAE-Sephadex A-50 (Pharmacia Corp.) or DEAE-Toyopearl (Toyosoda Co.), or molecular sieving means such as gel-filtration using Sephadex G-100, G-75 or Sephacryl S-200. These means can be used in combination. A purified powder of L-alanine dehydrogenase can be obtained by lyophilization with an added stabilizer, for example a sugar such as mannitol, saccharose or sorbitol, an amino acid such as glutamic acid or glycine, or a protein such as bovine serum albumin. The thus-obtained L-alanine dehydrogenase is quite stable in the solution.

The L-alanine dehydrogenase obtained has the following properties:

1. Molecular weight: 245,000±25,000 (gel-filtration method using a polyvinyl gel (trade name: TSK 3000 SW) (Toyosoda Co.) column, with a moving phase of 50 mM potassium phosphate buffer (pH 6.5) containing 0.2 M NaCl).

2. Isoelectric point: pH 4.6±0.5 (isoelectric focusing using a carrier ampholyte at 4° C., constant voltage at 700 V for 40 hours).

3. Km-Value
   0.84 mM (pyruvate)
   20.0 mM ($NH_4^+$)
   11.0 $\mu$M (NADH)

Figure 1:
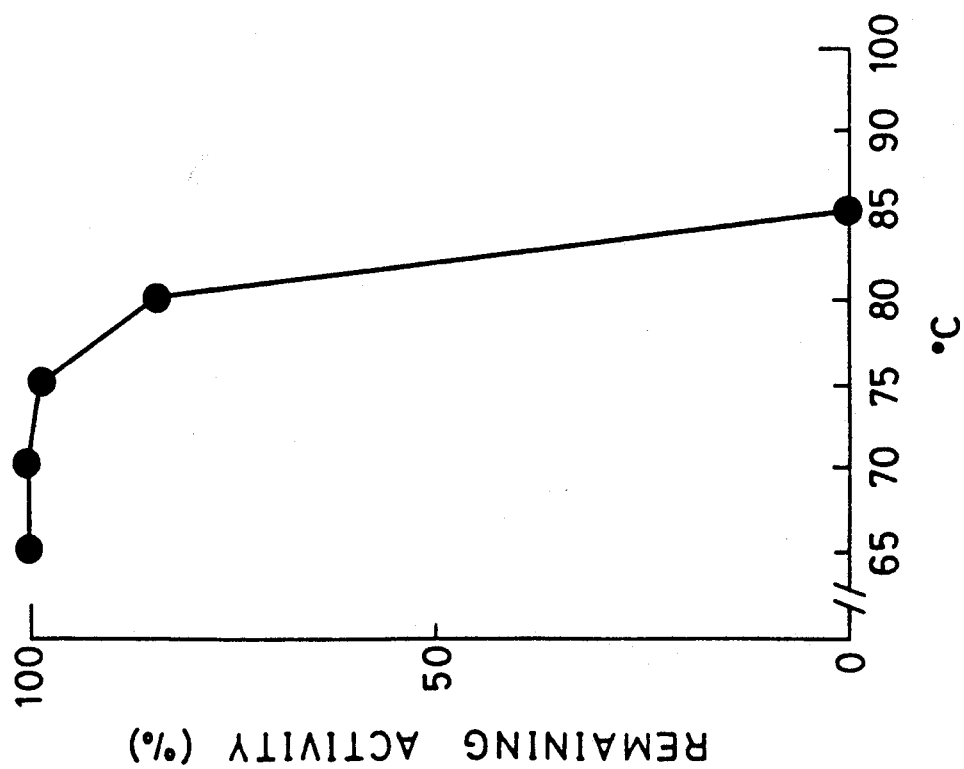
FIG. 1 is a graph of the heat stability of L-alanine dehydrogenase.

4. Heat stability: the enzyme solution (1.0 U/ml) is prepared in 20 mM Tris-HCl buffer (pH 8.0), heated for 15 mins., and the remaining enzymatic activity is measured by an enzymatic assay method given hereinbelow to obtain the results shown in FIG. 1. The enzyme is found to be stable up to at least 65° C.

5. Optimum temperature: enzyme activity is measured at each temperature shown in FIG. 2 according to an assay method illustrated hereinbelow by measuring optical absorption at 340 nm for decrease of NADH. As shown in FIG. 2, the enzyme shows maximum activity at 65° C.

6. pH stability: remaining activity of the enzyme (1.0 U/ml, 40 mM buffer solution) after heating at 80° C. for 15 mins. As shown in FIG. 3, the enzyme is stable at pH 6.0–7.5. In this figure: △=acetate buffer, pH 5.0–6.0; ○=phosphate buffer, pH 6.0–8.0; ●=Tris-HCl buffer, pH 7.5–9.0; □=glycine-NaOH buffer, pH 8.5–9.5.

7. Optimum pH: approx. pH 9.0 as shown in FIG. 4. Decrease at 340 nm for NADH with 40 mM buffer is measured according to an assay method given hereinbelow. In this figure: ○=phosphate buffer, pH 6.5–7.5; ●=Tris-HCl buffer, pH 7.5–9.0; □=glycine-NaOH buffer, pH 9.0–10.5.

The L-alanine dehydrogenase obtained by culturing the novel microorganism strain of the present invention, Sporolactobacillus sp. 78-3, was of high potency, and the culture and purification procedures were quite simple and easy.

Enzyme activity is measured by the following assay method:

Reaction mixture 50 mM triethanolamine
0.3 mM NADH
10 mM pyruvate acid
200 mM $NH_4Cl$
(pH 8.5)

Assay method

The reaction mixture, 1 ml, in a 1 ml quartz cell is pre-incubated at 37° C. for 5 mins. Dilute enzyme solution, 0.02 ml with 50 mM triethanolamine buffer (pH 8.5) is added thereto and the mixture is stirred to initiate the reaction. Decrease of NADH is measured photometrically at 340 nm during the reaction. Enzyme activity is calculated by the following equation on the linear part of the curve:

$$\text{Units/ml} = \frac{A}{6.22} \times \frac{1}{T} \times \frac{1.02}{0.02} \times X$$

wherein T=reaction time (min.); X=dilution ratio.

As illustrated hereinbefore, the present invention provides a high-efficiency process for the production of stable L-alanine dehydrogenase by using a novel L-alanine dehydrogenase-producing microorganism.

Furthermore, L-alanine dehydrogenase of the present invention can be used for quantitative analysis and assay according to the following enzymatic reaction:

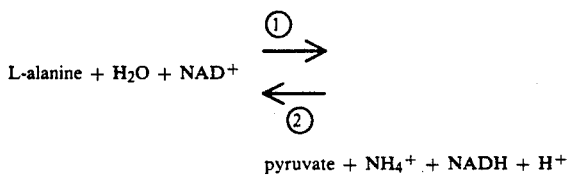

L-alanine + H$_2$O + NAD$^+$ ⇌ pyruvate + NH$_4^+$ + NADH + H$^+$

The optimum pH of the above oxidative deaminating reaction (①) is pH 10.5 and that of the reductive aminating reaction (②) is pH 9.0.

As can be clearly seen from the above reaction ①, alanine, a substrate of L-alanine dehydrogenase obtained by the present invention, can be quantitatively assayed by measuring NADH generation photometrically. Also pyruvate or ammonium ion can be assayed by measuring the decrease of NADH. Therefore, a direct assay of pyruvate or ammonium ion can be performed, and also the enzymatic activity of an enzyme which forms ammonium ion or pyruvate in the previous reaction, or substrates in the said previous reaction, can be assayed. Examples of enzymes which catalyze the formation of ammonium ion are as follows:

| | |
|---|---|
| E C. 3. 5. 1. 1 | Asparaginase |
| E C. 3. 5. 1. 2 | Glutaminase |
| E C. 3. 5. 1. 3 | ω-amidase |
| E C. 3. 5. 1. 4 | Amidase |
| E C. 3. 5. 1. 5 | Urease |
| E C. 3. 5. 1. 6 | β-ureidopropionase |
| E C. 3. 5. 1. 7 | Ureidopropinase |
| E C. 3. 5. 1. 12 | Biotinidase |
| E C. 3. 5. 1. 19 | Nicotinamidase |
| E C. 3. 5. 1. 20 | Citrullinase |
| E C. 3. 5. 1. 29 | α-(acetamidomethylene)succinate hydrolase |
| E C. 3. 5. 1. 30 | 5-aminovaleramidase |
| E C. 3. 5. 1. 35 | D-glutaminase |
| E C. 3. 5. 1. 38 | Glutamin-(asparagin)ase |
| E C. 3. 5. 1. 42 | Nicotinamidenucleotide amidase |
| E C. 3. 5. 1. 43 | Peptidyl-glutaminase |
| E C. 3. 5. 1. 44 | Glutaminyl-peptide glutaminase |
| E C. 3. 5. 1. 45 | Urease |
| E C. 3. 5. 3. 5 | Formiminoaspartate deiminase |
| E C. 3. 5. 3. 6 | Arginine deiminase |
| E C. 3. 5. 3. 7 | Guanidinobutyl tyrase |
| E C. 3. 5. 3. 9 | Allantoate deiminase |
| E C. 3. 5. 4. 1 | Cytosine deaminase |
| E C. 3. 5. 4. 2 | Adenine deaminase |
| E C. 3. 5. 4. 3 | Guanine deaminase |
| E C. 3. 5. 4. 4 | Adenosine deaminase |
| E C. 3. 5. 4. 5 | Cytidine deaminase |
| E C. 3. 5. 4. 6 | AMP deaminase |
| E C. 3. 5. 4. 7 | ADP deaminase |
| E C. 3. 5. 4. 8 | Aminoimidazolase |
| E C. 3. 5. 4. 11 | Pterin deaminase |
| E C. 3. 5. 4. 12 | dCMP deaminase |

-continued

| | |
|---|---|
| E C. 3. 5. 4. 13 | dCTP deaminase |
| E C. 3. 5. 4. 14 | Deoxycytidine deaminase |
| E C. 3. 5. 4. 15 | Guanosine deaminase |
| E C. 3. 5. 4. 17 | Adenosine (phosphate) deaminase |
| E C. 3. 5. 4. 18 | ATP deaminase |
| E C. 3. 5. 4. 20 | Pyrithiamin deaminase |
| E C. 3. 5. 4. 21 | Creatinine deaminase |
| E C. 3. 5. 4. 22 | 1-pyrroline 4-hydroxy 2-carboxylate deaminase |
| E C. 3. 5. 4. 23 | Blasticidin-S deaminase |
| E C. 3. 5. 4. 24 | Sepiapterin deaminase |
| E C. 3. 5. 5. 1 | Nitrilase |
| E C. 3. 5. 5. 2 | Ricinine nitrilase |
| E C. 3. 5. 5. 3 | Cyanate hydrolase |

For example, EC. 3. 5. 4. 4 adenosine deaminase has been assayed in the enzymatic reactions hereinbelow illustrated, by the method of Chaney & Marbach for ammonium ion which is introduced into the glutamate dehydrogenase (EC. 1. 4. 1. 3) reaction to measure the decrease of NADH. In that reaction, ammonium ion generated therein can be introduced into the enzymatic reaction of L-alanine dehydrogenase obtained by the present invention and the said adenosine deaminase can be assayed by photometric measurement of the decrease of NADH at 340 nm.

adenosine + H$_2$O → inosine + NH$_4^+$      (1)

pyruvate + NH$_4^+$ + NADH + H$^+$ → L-alanine + H$_2$O + NAD$^+$      (2)

The enzymatic activity of the enzyme which generates urea can be assayed by the reaction of urease with the generated urea and by the thus-formed ammonium ion being introduced into the L-alanine dehydrogenase system for direct measurement.

Examples of enzymes which form urea in the enzymatic reaction are as follows:

| | |
|---|---|
| E C. 3. 5. 2. 1 | Barbiturase |
| E C. 3. 5. 3. 1 | Arginase |
| E C. 3. 5. 3. 2 | Glycocyaminase |
| E C. 3. 5. 3. 3 | Creatinase |
| E C. 3. 5. 3. 4 | Allantoicase |
| E C. 3. 5. 3. 7 | Guanidinobutyrase |
| E C. 3. 5. 3. 10 | D-arginase |
| E C. 3. 5. 3. 11 | Agmatinase |
| E C. 3. 5. 3. 14 | Amidinoaspartase |

For example, in an assay of EC. 3. 5. 3. 1 arginase, urea generated in the following enzymatic reaction is treated with urease and the ammonium ion thus formed is introduced into the enzymatic reaction of L-alanine dehydrogenase in the present invention and is measured photometrically as the decrease of NADH at 340 nm.

arginine + H$_2$O → lysine + urea      (1)

ATP + urea + H$_2$O → ADP + pi + CO$_2$ + 2NH$_4^+$      (2)

pyruvate + NH$_4^+$ + NADH + H$^+$ → L-alanine + H$_2$O + NAD$^+$

As illustrated hereinabove, various kinds of analyses and assays can be performed by using L-alanine dehydrogenase.

The following examples illustrate the present invention but are not to be construed as limiting:

EXAMPLE 1

| (i) peptone (Kyokuto Seiyaku Co.) | 1.0% |
|---|---|
| yeast extract (Kyokuto Seiyaku Co.) | 0.5% |
| glucose | 1.0% |
| alanine | 2.0% |
| $KH_2PO_4$ | 0.3% |
| $MgSO_4.7H_2O$ | 0.05% |
| $CaCl_2.2H_2O$ | 0.02% |
| (pH 7.0) | |

A liquid medium (100 ml) comprising the above composition in a 500 ml Erlenmeyer flask was sterilized at 120° C. for 20 mins. One loopful of Sporolactobacillus sp. 78-3 was inoculated into the medium and the medium was cultured at 50.C. at 120 rpm for 24 hours to obtain the cultured mass (100 ml) (relative activity: 50 U/ml).

| (ii) polypeptone (Takeda Chem. Ind.) | -1.0% |
|---|---|
| yeast extract (Kyokuto Seiyaku Co.) | 0.2% |
| soluble starch | 1.0% |
| alanine | 2.0% |
| $KH_2PO_4$ | 0.3% |
| $MgSO_4.7H_2O$ | 0.05% |
| $CaCl_2.2H_2O$ | 0.02% |
| (pH 7.0) | |

The liquid medium (20 l) comprising the above composition in a 30 l jar fermenter was sterilized by heating. The precultured seed culture obtained in (i) hereinabove (100 ml) was inoculated therein and the mixture was cultured at 50° C., with aeration of 20 l/min., inner pressure 0.2 kg/cm², and agitation at 120 rpm for 16 hours to obtain the cultured mass (19 l).

EXAMPLE 2

Purification of enzyme:

Bacterial cells collected by centrifugation from the cultured broth (19 l) obtained in Example 1, Culture (ii), were suspended in 40 mM phosphate buffer (pH 7.0) and mixed with 0.1% lysozyme (5 l) and solubilized at 37° C. for 30 mins.; then the mixture was adjusted to pH 7.0 and heated at 70° C. for 30 mins. After immediate cooling of the mixture, a precipitate was centrifugally removed to obtain a supernatant solution (4500 ml) (enzyme activity: 304 U/ml). An equal amount of acetate was added to the supernatant solution, which was mixed well by stirring and then centrifuged to separate the precipitate. 40 mM phosphate buffer (pH 7.0) (1 l) was added to the precipitate, the material was stirred, and the sediment was removed by centrifugation to obtain a supernatant solution. The supernatant solution was passed through a column of DEAE-Sepharose CL-6B (Pharmacia Corp.) (500 ml). The enzyme solution was eluted with 40 mM phosphate buffer (pH 7.0) (500 ml) containing 0.2 M KCl, then ammonium sulfate (156 g) was added thereto, and the mixture was stirred and centrifuged to separate the precipitate. Ammonium sulfate (35 g) was added to a solution of this precipitate dissolved in 40 mM phosphate buffer solution (pH 7.0) (200 ml), up to ammonium sulfate 30% saturation, and the resulting material was passed through a column of Octylsepharose CL-4B (Pharmacia Corp.) (100 ml), buffered with 30% saturated ammonium sulfate. The column was washed with the same buffer solution (500 ml), then the 20% saturated ammonium sulfate (200 ml) was passed therethrough to obtain the enzyme solution. The thus-obtained enzyme solution was dialyzed twice against 40 mM phosphate buffer solution (pH 7.0) (10 l) overnight to yield an enzyme solution 250 ml (enzyme activity: 2750 U/ml, recovery: 50.3%).

EXAMPLE 3

Assay of ammonium ion using L-alanine dehydrogenase:

| Reaction mixture: | |
|---|---|
| Tris-HCl buffer (pH 8.5) | 50 mM |
| NADH (Oriental Yeast Co.) | 0.2 mM |
| Sodium pyruvate | 10 mM |
| L-alanine dehydrogenase | 3.75 U |

Figure 5:
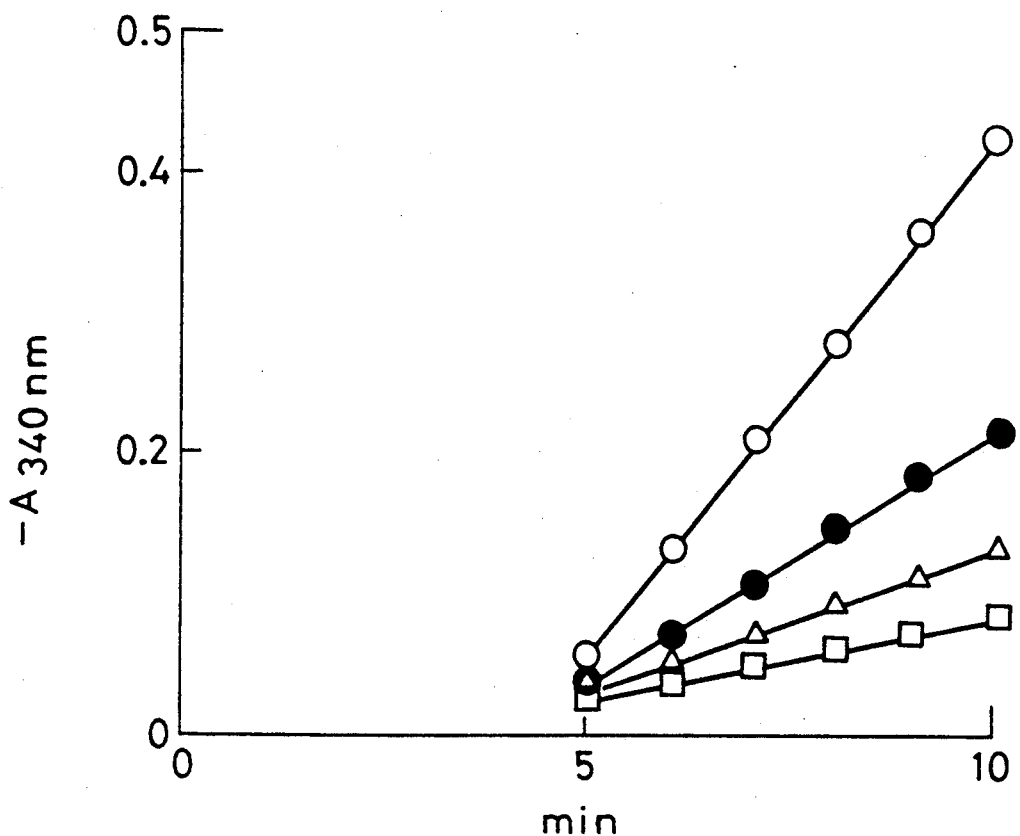
FIG. 5 is a rate assay of ammonium ion upon altering NH$_4$Cl concentration.
Figure 6:
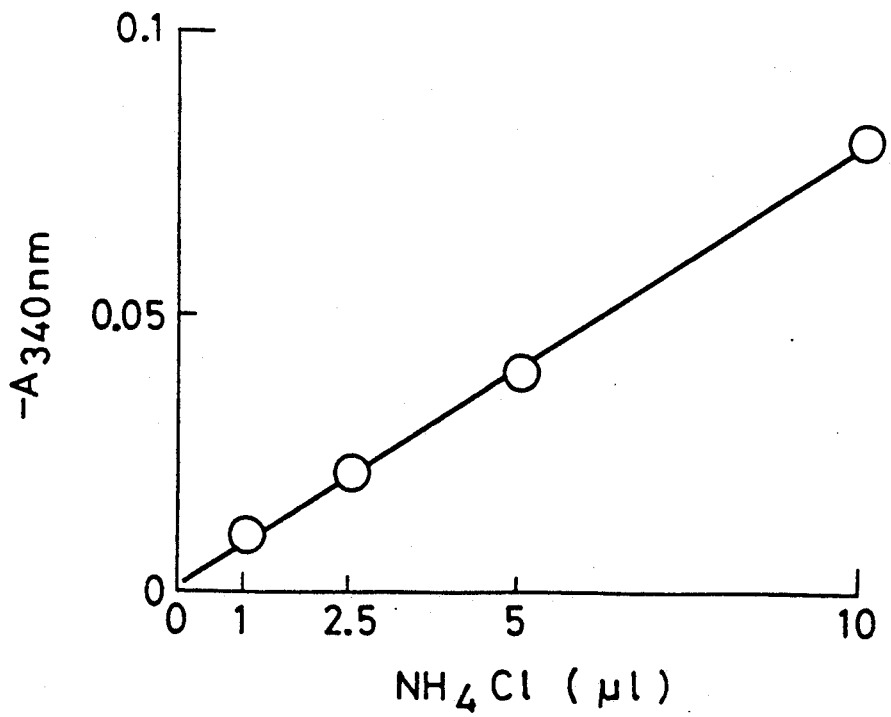
FIG. 6 is the assay curve of ammonium ion.

10 mM $NH_4Cl$ was added to the above reaction mixture (1 ml). In FIG. 5: □ = 1 μl of 10 mM $NH_4Cl$, Δ = 2.5 μl; ● = 5 μl and O = 10 μl, respectively. The decrease in optical density at 340 nm was measured. The decrease in optical density at 340 nm within the one minute between the 7th and 8th mins. is shown in FIG. 6, in which the curve is linear from the point of origin.

EXAMPLE 4

Assay of urea using L-alanine dehydrogenase:

| Reaction mixture: | |
|---|---|
| Tris-HCl buffer (pH 8.5) | 50 mM |
| NADH (Oriental Yeast Co.) | 0.2 mM |
| Sodium pyruvate | 10 mM |
| L-alanine dehydrogenase | 5.0 U |
| Urease (jack beans) | 25 U |

Figure 7:
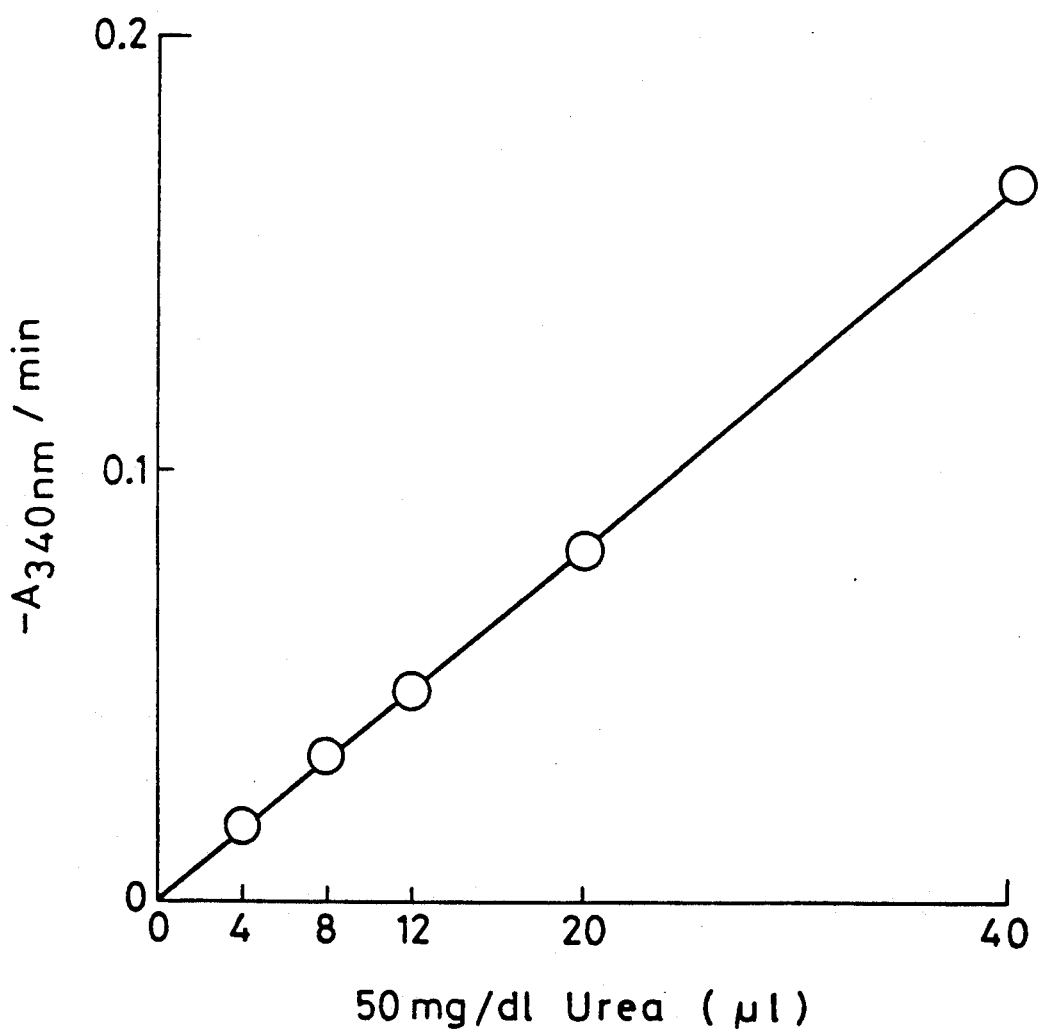
FIG. 7 is the assay curve or urea.

Quantities of 4 μl, 8 μl, 12 μl, 20 μl and 40 μl, respectively of urea solution (50 mg/dl) were added to the reaction mixture (3 ml) hereinabove. The decrease in optical density at 340 nm was measured. The decrease within the one minute between the 7th and 8th mins. is shown in FIG. 7, wherein again it will be noted that the curve is linear from the point of origin.

EXAMPLE 5

Measurement of adenosine deaminase activity using L-alanine dehydrogenase:

| Reaction mixture: | |
|---|---|
| Tris-HCl buffer (pH 8.5) | 50 mM |
| NADH (Oriental Yeast Co.) | 0.2 mM |
| Sodium pyruvate | 10 mM |
| L-alanine dehydrogenase | 20.0 U |

Figure 8:
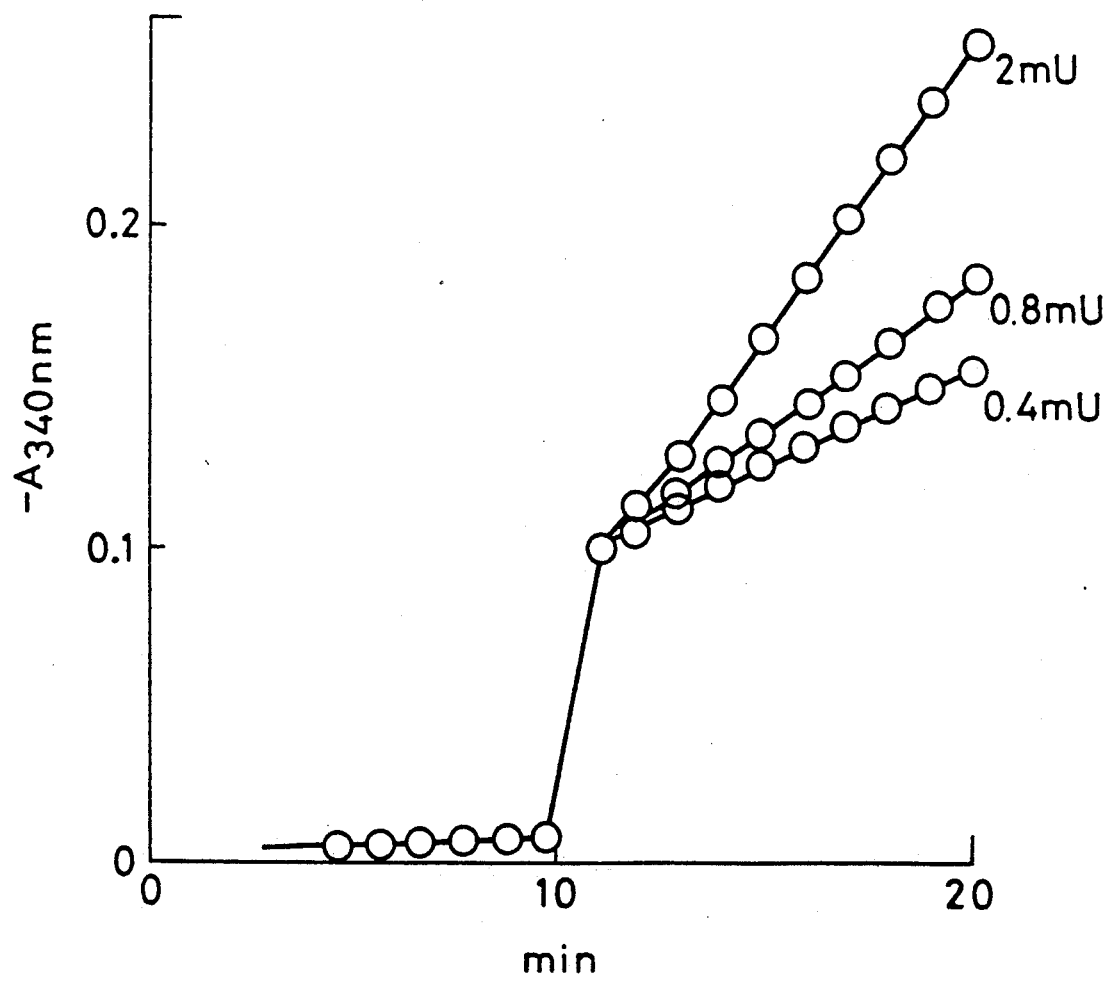
FIG. 8 is a rate assay of adenosine deaminase upon altering the concentration of adenosine deaminase.
Figure 9:
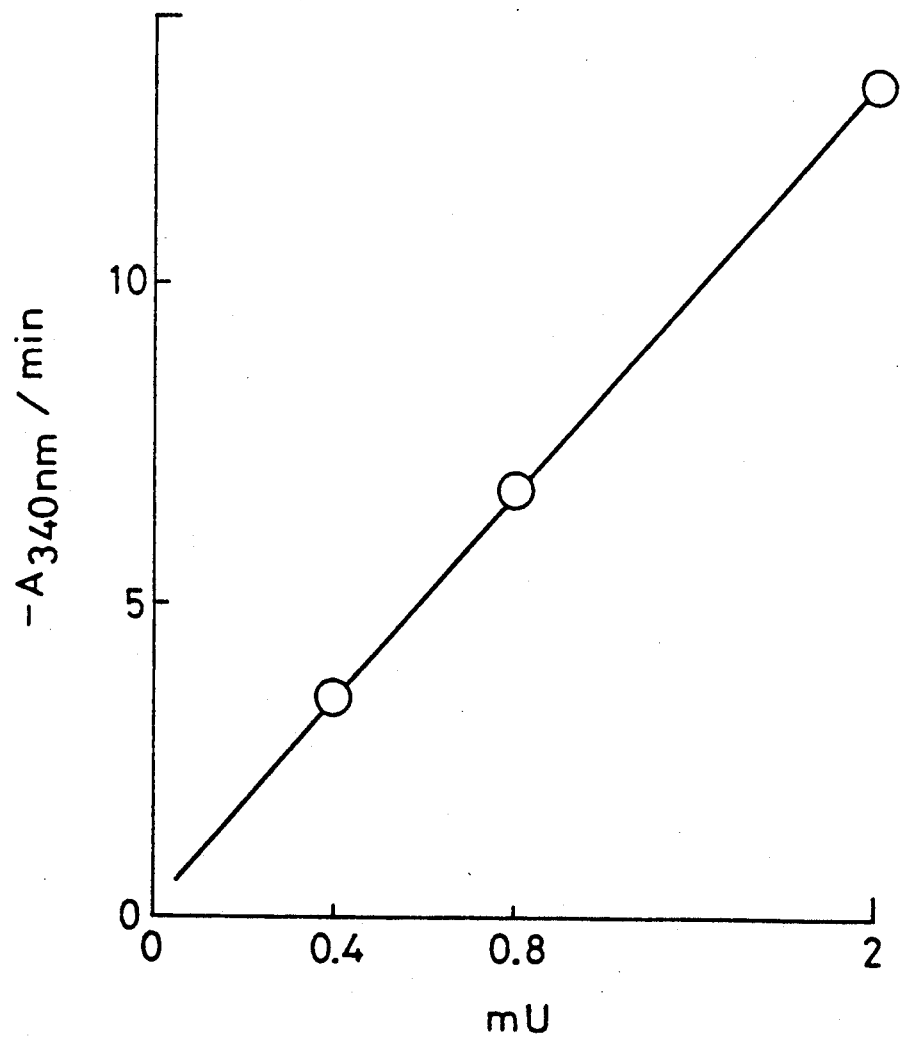
FIG. 9 is a standard curve of adenosine deaminase.

Adenosine deaminase quantities of 0.4 mU, 0.8 mU and 2 mU, respectively, were added to the above reaction mixture (1 ml) and the mixtures were incubated at 37° C. for 10 mins. 1 mM adenosine (100 μl) was added to each reaction mixture, and the decrease in optical density at 340 nm was measured. The results are shown in FIG. 8. In FIG. 9, the decrease at 340 nm within the one minute between the 16th and 17th mins. is shown. Good linearity is obtained.

In the assay systems hereinabove illustrated, the pH of the reaction buffer is pH 8-10, preferably 8.5-9.5. The concentration of NADH is 0.01 mM-0.6 mM, preferably 0.2-0.3 mM.

The concentration of pyruvate is 0.5 mM-0.5 M, preferably 5-20 mM.

The concentration of L-alanine dehydrogenase is 0.1-500 U/ml, preferably 10-30 U/ml.

If required, a lactic acid dehydrogenase (LDH) inhibitor such as oxaminic acid or oxalic acid, in an amount of 10-70 mM, can be added for the prevention of the effects of serum LDH.

Thus by the present invention, a process for the production of L-alanine dehydrogenase of high potency is provided.

What is claim is:

1. A process for the production of L-alanine dehydrogenase which comprises culturing Sporolactobacillus sp. 78-3 FERM BP-2517 in a nutrient medium and recovering said L-alanine dehydrogenase.

* * * * *